United States Patent

Rehnig et al.

[11] Patent Number: 5,968,964
[45] Date of Patent: Oct. 19, 1999

[54] FUNGICIDAL LIQUID FORMULATION

[75] Inventors: Annerose Rehnig, Ingelheim, Germany; Jean Claude Bozier, Bron; Xavier Veyrand, Mizérieux, both of France

[73] Assignee: American Cyanamid Company, Madison, N.J.

[21] Appl. No.: 09/108,762

[22] Filed: Jul. 1, 1998

[51] Int. Cl.[6] .......................... A01N 43/50; A01N 43/64
[52] U.S. Cl. .......................... 514/383; 514/396; 514/399
[58] Field of Search ...................................... 514/383, 396, 514/399

[56] References Cited

U.S. PATENT DOCUMENTS

| | | | |
|---|---|---|---|
| 4,938,792 | 7/1990 | Kumazawa et al. | 548/262.2 |
| 5,393,770 | 2/1995 | Grayson | 514/313 |

OTHER PUBLICATIONS

The Pesticide Manual, 10th Edition, 1994, pp. 193–195 and 669–670.

Primary Examiner—Allen J. Robinson
Attorney, Agent, or Firm—John W. Hogan, Jr.

[57] ABSTRACT

The invention relates to a liquid fungicidal composition comprising (a) a fungicidally acceptable carrier comprising a mixture of 1-pentanol and 2-methylbutanol, wherein the ratio (by weight) of the 1-pentanol to 2-methylbutanol is from 1:1 to 1:10;
(b) at least one compound of formula I,

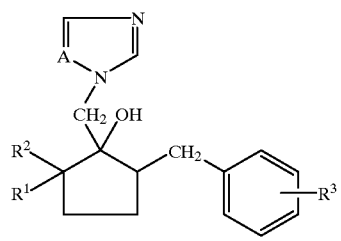

(I)

in which

R[1] and R[2] each independently represent hydrogen atom or an optionally substituted alkyl, alkenyl, alkynyl or alkadienyl group;

R[3] represents a halogen atom or an optionally substituted alkyl, alkenyl, alkynyl, alkadienyl, alkoxy or aryl group;

A represents a nitrogen atom or a CH group; or one of the salts or addition products thereof, which exists in solubilized form;

(c) a solubilizing agent; and
(d) optionally other formulation adjuvants.

10 Claims, No Drawings

FUNGICIDAL LIQUID FORMULATION

BACKGROUND OF THE INVENTION

The present invention relates to certain liquid fungicidal compositions.

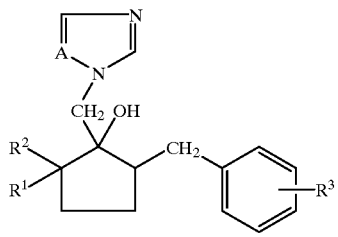

are known from U.S. Pat. No. 4,938,792.

U.S. Pat. No. 5,393,770 discloses liquid concentrated fungicidal compositions comprising compounds of formula I, solubilizing agents and 1-pentanol. CARAMBA™ SL 60 fungicide contains metconazole as an active ingredient, a solubilizing agent and a mixture of 1-pentanol with different branched pentanols (2-methylbutanol and 3-methylbutanol) wherein the ratio (by weight) of the 1-pentanol to the branched pentanols is about 7:3. However, these formulations are not entirely satisfactory with respect to their crop tolerance. In particular, if the formulation is applied in high dose rates and in a short interval of about one week, some injury to certain crops, in particular wheat, has been observed.

SUMMARY OF THE INVENTION

Surprisingly, it has been found that fungicidal compositions which comprise a compound of formula I, a solubilizing agent, and a mixture of 2-methylbutanol and 1-pentanol, wherein the ratio (by weight) is at least 1:1 represent improved formulations which can be applied even in high dose rates and in an interval of about one week with increased crop safety.

Therefore, the present invention relates to a liquid fungicidal composition comprising (a) a fungicidally acceptable carrier comprising a mixture of 2-methylbutanol and 1-pentanol, wherein the ratio (by weight) of the 1-pentanol to 2-methylbutanol is from 1:1 to 1:10;
(b) at least one azole derivative of formula I

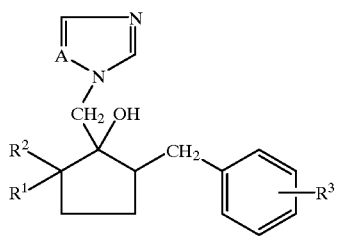

in which
$R^1$ and $R^2$ each independently represent hydrogen atom or an optionally substituted alkyl, alkenyl, alkynyl or alkadienyl group;
$R^3$ represents a halogen atom or an optionally substituted alkyl, alkenyl, alkynyl, alkadienyl, alkoxy or aryl group;
A represents a nitrogen atom or a CH group; or one of the salts or addition products thereof; which exists in dissolved form;
(c) a solubilizing agent; and
(d) optionally other formulation adjuvants.

The present invention also includes a method for controlling phytopathogenic fungi which comprises the application of the liquid formulation of the invention or a spray mix obtained from the liquid formulation described above.

DETAILED DESCRIPTION OF THE PREFERRED EMBODIMENTS

Preferred azoles of formula I are those wherein A represents a nitrogen atom; $R^1$ and $R^2$ represent a $C_{1-6}$ alkyl group, preferably a methyl group; and $R^3$ is attached in the para-position and represents a fluoro or chloro atom or a $C_{1-6}$ haloalkyl group.

In particular metconazole is an especially preferred compound having formula IA:

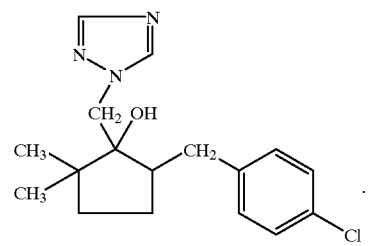

Metconazole is known from "The Pesticide Manual", 10th Edition, The British Crop Protection Council and The Royal Society of Chemistry, 1994, (hereinbelow abbreviated as "Pesticide Manual"), page 669.

A composition according to the invention preferably contains from (w/w) of the active ingredient of formula I.

The compound of formula I is capable of forming salts or addition products with inorganic or organic acids or metal ions. However, the active ingredient of formula I is preferably not a salt.

Examples of inorganic acids are hydrohalides like hydrofluoric acid, hydrochloric acid, hydrobromic acid and hydroiodic acid and additionally sulfuric acid, phosphoric acid and nitric acid.

Suitable organic acids are formic acid and alkanoic acids such as acetic acid, trifluoroacetic acid, trichloroacetic acid and propionic acid, and additionally glycolic acid, lactic acid, succinic acid, citric acid, benzoic acid, cinnamic acid, oxalic acid, alkylsulfonic acids, arylsulfonic acids, alkylphosponic acids, arylphosphonic acids, in which the alkyl and/or aryl moieties are optionally substituted, as for example para-toluenesulfonic acid, salicylic acid, para-phenoxybenzoic acid, 2-acetoxybenzoic acid or the like.

The ions of the metals which represent soft Lewis acids are suitable for forming addition products, preferably ions of chromium, manganese, iron, cobalt, nickel, copper, zinc, calcium and magnesium, aluminium, tin and lead.

Fungicidally acceptable carriers are as a rule liquid carriers, preferably organic solvents or a mixture thereof. The liquid carrier of the present invention contains preferably one or more co-solvents in addition to the solvent mixture of 1-pentanol and 2-methylbutanol. These co-solvents are preferably aromatic hydrocarbons, e.g. Solvesso® 200, substituted naphthalenes, phthalic acid esters, such as dibutyl or dioctyl phthalate, aliphatic hydrocarbons, e.g. cyclohexane or Shellsol® TD or paraffins, alcohols and glycols as well as their ethers and esters, e.g. ethanol, ethyleneglycol mono- and dimethyl ether, ketones such as cyclohexanone, strongly polar solvents, preferably alkyl pyrrolidones such as N-methyl-2-pyrrolidone, n-octylpyrrolidone or cyclohexylpyrrolidone, or γ-butyrolactone, epoxidized plant oil esters, e.g. methylated coconut or soybean oil ester and water. Mixtures of different liquids are often suitable.

In a preferred embodiment of the present invention the liquid carrier consists essentially of a mixture of 1-pentanol and 2-methylbutanol, and a non-polar organic co-solvent.

Suitably the ratio (by weight) of the 1-pentanol to 2-methylbutanol is from 1:1 to 1:10. Preferably the ratio (by weight) of the 1 -pentanol to 2-methylbutanol is from 1:1 to 1:5, in particular from 49:51 to 40:60.

It is also preferred that liquid compositions containing metconazole contain little, if any, 3-methylbutanol. Compositions essentially free of 3-methylbutanol are a preferred embodiment of the invention.

In a particularly preferred embodiment the mixture of 1-pentanol and 2-methylbutanol is a commercially available product which contains 50% to 55% by weight of 2-methylbutanol, in particular Pentanol 45, which is commercially available from Clariant GmbH.

The compositions of this invention can also comprise also other compounds having biological activity, e.g. compounds having similar or complementary fungicidal activity or compounds having plant growth regulating, herbicidal or insecticidal activity.

The other fungicidal compound can be, for example, one which is capable of combating diseases of cereals (e.g. wheat) such as those caused by Erysiphe, Puccinia, Septoria, Gibberella, Fusarium and Helminthosporium spp., seed and soil borne diseases and downy and powdery mildews on vines and powdery mildew and scab on apples etc. These mixtures of fungicides can have a broader spectrum of activity than the compound of general formula I alone.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclomezine, diethofencarb, difenoconazole, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, methfuroxam, myclobutanil, neoasozin, nickel dimethyidithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram.

The compounds of formula I exhibit an extraordinary efficacy against a broad range of phytopathogenic fungi, in particular against fungi from the classes Ascomycetes, Basidiomycetes, Phycomycetes and Deuteromycetes. They are systemic and may be applied as leaf or soil fungicides.

The compositions according to the invention may be preferably applied for controlling the following phytopathogenic fungal species of the genera: Alternaria, Botrytis, Cercospora, Colletotrichum, Erysiphe (Blumeria), Elsinoe, Fusarium, Gibberella, Guignardia, Helminthosporium, Hemileia, Monilinia, Mycosphaerella, Nectria, Phythium, Phytophthora, Plasmopara, Podosphaera, Pseudocercosporella, Pseudoperonospora, Puccinia, Pyrenophora, Pyricularia, Rhizoctonia, Sclerotinia, Sclerotium, Septoria, Sphaerotheca, Tilletia, Typhula, Uncinula, Uromyces, Ustilago, Venturia, Verticilium and others.

The application rate of the compound of formula I according to this invention is usually in the range of 1 to 500 grams of active ingredient per hectare (g a.i./ha), with rates between 15 to 200 g a.i./ha often achieving satisfactory control. The optimal rate for a specific application will depend on the crop(s) under cultivation and the predominant species of infesting fungus, and readily may be determined by established biological tests known to those skilled in the art.

The solubilizing agent is a surfactant preferably from the group of alkoxylates of aliphatic alcohols. Preferred alkoxylates of an aliphatic alcohol are those based on alkoxy units having 2 carbon, or 2 and 3 carbon atoms (i.e. being a mixed ethoxylate or being a mixed ethoxylate/propoxylate). In a preferred aliphatic alcohol alkoxylate, the alkoxylate chain may have at least 5 alkoxy moieties, suitably from 5 to 25 alkoxy moities, preferably 5 to 15, in particular 5 to 9. The alcohol moiety is as a rule derived from a $C_{9-18}$ aliphatic alcohol. Preferred alcohols are at least 50% by weight primary and at least 50% by weight straight chain alcohols and with at least 50% by weight having one hydroxy group.

Particularly preferred are NEODOL® (former DOBANOL®) alcohol ethoxylates from Shell Chemical Co. Ltd.

In a preferred embodiment of the present invention the weight ratio of the solubilizing agent to the compound of formula I is in the range of from 2:1 to 20:1, preferably from 5:1 to 15:1, in particular from 6:1 to 10:1.

In a preferred embodiment of the present invention the weight ratio of the fungicidal active ingredient of formula I to the liquid carrier is in the range of from 1:1 to 1:20, preferably from 1:5 to 1:15, in particular about 1:10. The liquid carrier is composed of all of the solvent(s), solvent mixtures, and/or co-solvent(s).

Preferred are liquid formulations, comprising the following constituents:

a mixture consisting essentially of 10 to 50% by weight of 1-pentanol, and 50 to 90% by weight of 2-methylbutanol;

an azole derivative of formula I, in particular metconazole;

a solubilizing agent, e. g. an alkoxylate of an aliphatic alcohol being an ethoxylate or a mixed ethoxylate/ propoxylate composed of 5 to 25 alkoxy moieties, in particular NEODOL® alcohol ethoxylates, which are commercially available from Shell Chemical Co. Ltd.; and a co-solvent which has foam breaking properties, preferably a mixture of aliphatic hydrocarbons, in particular Shellsol® TD, which is commercially available from Shell Chemical Co. Ltd.

In a preferred embodiment of this invention the liquid co-formulation consists essentially of 0.5 to 15%, preferably 2 to 10% by weight of an azole derivative of formula I;

20 to 70%, preferably 30 to 50% by weight of a solubilizing agent, 5 to 40%, preferably 10 to 30% by weight of a co-solvent having foam breaking properties;

10 to 60%, preferably 20 to 50% by weight of a solvent mixture consisting essentially of 30 to 50% by weight of 1-pentanol and 50 to 70% by weight of 2-methylbutanol;

and the sum of all ingredients in the composition is 100%.

A method of making such a composition is also provided which comprises bringing a compound of formula I into association with the carrier. It is also envisaged that different isomers or mixtures of isomers of formula I may have different levels or spectra of activity and thus compositions may comprise individual isomers or mixtures of isomers.

Pesticidal compositions are often formulated and transported in a concentrated form which is subsequently diluted by the user before application. The presence of small amounts of a surfactant in the composition facilitates this process of dilution. The compositions of the invention optionally include formulation adjuvants such as surfactants.

Surfactants may be nonionic, anionic, cationic or zwitterionic substances with good dispersing, emulsifying and wetting properties depending on the nature of the compound according to general formula I to be formulated. Surfactant may also mean mixtures of individual surfactants.

The compositions of the invention may be formulated as soluble liquid (SL) compositions. They may contain 0 to 10% w/v of other formulation adjuvants such as defoamers, corrosion inhibitors, stabilizers, penetrants and stickers, and water. Certain organic solids or inorganic salts may be present, dissolved in the formulation, to assist in preventing sedimentation and crystalization or as antifreeze agents for water.

Aqueous dispersions and emulsions, for example compositions obtained by diluting the formulated product according to the invention with water, also lie within the scope of the invention.

The biological activity of the active ingredient can also be increased by including an adjuvant in the spray dilution. The adjuvant can either be included in the formulation as a coformulant, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.001 to 10 kg a.i./ha, preferably 0.03 to 0.5 kg a.i./ha, in particular 0.04 to 0.4 kg a.i./ha.

Examples of formulations according to the invention are:

| Component | Function | Concentration |
|---|---|---|
| Formulation A | | |
| Metconazole | Active Ingredient | 60 g/l |
| NEODOL ® 91-6[1) $C_9$–$C_{11}$ alcohol ethoxylate | Solubilizing Agent | 400 g/l |
| Shellsol ® TD[1) aliphatic hydrocarbon | Co-solvent/ Defoamer | 200 g/l |
| Pentanol 45[2) mixture of 1-pentanol and 2-methylbutanol (47:53) | Solvent | to 1 l |
| Formulation B | | |
| Metconazole | Active Ingredient | 90 g/l |
| NEODOL ® 91-6[1) | Solubilizing Agent | 600 g/l |
| Shellsol ® TD[1) aliphatic hydrocarbon | Co-solvent/ Defoamer | 200 g/l |
| Pentanol 45[2) mixture of 1-pentanol and 2-methylbutanol (47:53) | Solvent | to 1 l |

[1)available from Shell Chemical CO., Ltd.
[2)available from Clariant GmbH

The following examples illustrate specific embodiments of the present invention; however, the invention is not limited to the embodiments so illustrated, but includes the entire scope of the appended claims.

EXAMPLES

Effect of CARAMBA® (60 g/l metconazole) comprising 1-pentanol and different branched pentanoles (70:30) as solvent, and a metconazole/ 60 g/l SL formulation (Formulation A) comprising a mixture of 1-pentanol and 2-methylbutanol (47:53) as solvent against cereal diseases.

Selectivity tests with five different wheat varieties were carried out in a greenhouse to investigate phytotoxicity of Formulation A and the commercial formulation CARAMBA SL 60.

CARAMBA SL 60 and Formulation A were applied to the test plants at the normal field dose rate (N=1.5 l/ha product) as well as the double (2 N) field dose rate in 200 I water/ha using a track sprayer.

The results showed that both the Formulation A containing 1-pentanol and 2-methylbutanol (47:53) as solvent and CARAMBA SL 60 containing 1-pentanol and branched pentanols (70:30) as solvent were selective in wheat plants under greenhouse conditions 6 days after the first application of each product.

After two applications (second application 6 days after the first) and at a higher dose rate (2N) Formulation A is surprisingly more selective than CARAMBA SL 60.

Methodology of the Tests

The products were applied to the foliage of wheat plants with 200 l water/ha using an even-spray-nozzle track sprayer. Prior to the application, the test products were diluted with demineralized water to give the final concentrations of N (normal field rate, CARAMBA SL 60 g/l is applied at 1.5 l/ha product) and 2 N (two-fold field rate). Dose rates higher than the normal field rate were used in order to provoke phytotoxicity in wheat plants. For this reason, the test plants were also treated twice at an interval of seven days because no or insignificant phytotoxicity was observed six days after the first treatment.

Test Plants

The study included five wheat varieties: 'Herzog' (winter wheat), 'Monopol' (winter wheat), 'Kanzler' (winter wheat), 'Ralle' (spring wheat), and 'Apollo' (winter wheat). The plants were treated in their six to eight leaf stage. Each treatment included four replicated pots, each pot with 8–10 plants.

Evaluation

The test plants were assessed for phytotoxic symptoms six (6 d*) and eleven days (11 d*) after the first treatment (eleven days after the first treatment=four days (4 d**) after the second treatment). The plants were evaluated for visible phytotoxic symptoms like necrosis, chlorosis, stunting, deformations, wilting, bleaching, and bronzing.

The level of phytotoxicity was assessed according to a 0 to 5 scale where

'0' was 'not phytotoxic=full selective',

'1' was 'traces of phytotoxicity=acceptable in practice',

'2' was 'slight phytotoxicity=almost acceptable in practice but critical',

'3' was 'moderate phytotoxicity=not acceptable in practice',

'4' was 'severe phytotoxicity=not acceptable in practice', and

'5' was 'extreme phytotoxicity or death plants=not acceptable in practice'.

The influence on different leaves [a]° treated leaves and b) °° new leaves=leaves emerged after treating the plant] as well as on different parts of treated leaves [leaf apex and leaf lamina] was differentiated.

The test plants of each pot were evaluated separately. The tables of results (Tables I to V) present mean values calculated from four replicates.

TABLE I

Selectivity of CARAMBA SL 60 and of Formulation A on wheat plants of the variety "Herzog" after one (*) and two (**) applications

| Application: Track sprayer, 200 l/ha | | Dose rate (g ai/ha) | "Herzog" Necrosis or Chlorosis | |
|---|---|---|---|---|
| | | | 6 d* | 4 d**(=11 d*) |
| CARAMBA SL 60 | Leaf apex° | 180 | 0.0 | 0.5 |
| | leaf lamina° | | 0.0 | 2.0 |
| | New leaves°° | | 0.0 | 0.3 |
| | Leaf apex° | 90 | 0.0 | 0.3 |
| | Leaf lamina° | | 0.0 | 0.8 |
| | New leaves°° | | 0.0 | 1.0 |
| FORMULATION A | Leaf apex° | 180 | 0.0 | 0.3 |
| | Leaf lamina° | | 0.0 | 0.8 |
| | New leaves°° | | 0.3 | 0.3 |
| | Leaf apex° | 90 | 0.0 | 0.0 |
| | Leaf lamina° | | 0.0 | 0.0 |
| | New leaves°° | | 0.0 | 0.0 |

TABLE II

Selectivity of CARAMBA SL 60 and of Formulation A on wheat plants of the variety "Apollo" after one (*) and two (**) applications

| Application: Track sprayer, 200 l/ha | | Dose rate (g ai/ha) | "Apollo" Necrosis or Chlorosis | |
|---|---|---|---|---|
| | | | 6 d* | 4 d**(=11 d*) |
| CARAMBA SL 60 | Leaf apex° | 180 | 0.0 | 2.8 |
| | Leaf lamina° | | 0.3 | 3.8 |
| | New leaves°° | | 0.0 | 1.0 |
| | Leaf apex° | 90 | 0.3 | 0.5 |
| | Leaf lamina° | | 0.0 | 1.0 |
| | New leaves°° | | 0.0 | 0.5 |
| FORMULATION A | Leaf apex° | 180 | 0.0 | 1.0 |
| | Leaf lamina° | | 0.3 | 2.8 |
| | New leaves°° | | 0.0 | 0.8 |

TABLE II-continued

Selectivity of CARAMBA SL 60 and of Formulation A on wheat plants of the variety "Apollo" after one (*) and two (**) applications

| Application: Track sprayer, 200 l/ha | | Dose rate (g ai/ha) | "Apollo" Necrosis or Chlorosis | |
|---|---|---|---|---|
| | | | 6 d* | 4 d**(=11 d*) |
| | Leaf apex° | 90 | 0.3 | 0.3 |
| | Leaf lamina° | | 0.0 | 0.0 |
| | New leaves°° | | 0.0 | 0.0 |

TABLE III

Selectivity of CARAMBA SL 60 and of Formulation A on wheat plants of the variety "Kanzler" after one (*) and two (**) applications

| Application: Track sprayer, 200 l/ha | | Dose rate (g ai/ha) | "Kanzler" Necrosis or Chlorosis | |
|---|---|---|---|---|
| | | | 6 d* | 4 d**(=11 d*) |
| CARAMBA SL 60 | Leaf apex° | 180 | 0.0 | 1.3 |
| | Leaf lamina° | | 0.0 | 2.5 |
| | New leaves°° | | 0.5 | 1.5 |
| | Leaf apex° | 90 | 0.0 | 0.0 |
| | Leaf lamina° | | 0.0 | 0.0 |
| | New leaves°° | | 0.0 | 1.0 |
| FORMULATION A | Leaf apex° | 180 | 0.0 | 0.0 |
| | Leaf lamina° | | 0.0 | 1.5 |
| | New leaves°° | | 0.3 | 0.8 |
| | Leaf apex° | 90 | 0.0 | 0.0 |
| | Leaf lamina° | | 0.0 | 0.0 |
| | New leaves°° | | 0.5 | 0.5 |

TABLE IV

Selectivity of CARAMBA SL 60 and of Formulation A on wheat plants of the variety "Monopol" after one (*) and two (**) applications

| Application: Track sprayer, 200 l/ha | | Dose rate (g ai/ha) | "Monopol" Necrosis or Chlorosis | |
|---|---|---|---|---|
| | | | 6 d* | 4 d**(=11 d*) |
| CARAMBA SL 60 | Leaf apex° | 180 | 0.0 | 2.5 |
| | Leaf lamina° | | 0.3 | 3.5 |
| | New leaves°° | | 1.0 | 1.0 |
| | Leaf apex° | 90 | 1.0 | 1.0 |
| | Leaf lamina° | | 0.0 | 1.5 |
| | New leaves°° | | — | 1.0 |
| FORMULATION A | Leaf apex° | 180 | 0.5 | 0.5 |
| | Leaf lamina° | | 0.3 | 0.5 |
| | New leaves°° | | 1.0 | 1.0 |
| | Leaf apex° | 90 | 0.3 | 1.0 |
| | Leaf lamina° | | 0.0 | 1.8 |
| | New leaves°° | | 1.0 | 1.0 |

TABLE V

Selectivity of CARAMBA SL 60 and of Formulation A on wheat plants of the variety "Ralle" after one (*) and two (**) applications

| Application: Track sprayer, 200 l/ha | | Dose rate (g ai/ha) | "Ralle" Necrosis or Chlorosis | |
|---|---|---|---|---|
| | | | 6 d* | 4 d**(=11 d*) |
| CARAMBA SL 60 | Leaf apex° | 180 | 0.3 | 3.5 |
| | Leaf lamina° | | 0.0 | 3.5 |
| | New leaves°° | | 0.0 | 1.0 |
| | Leaf apex° | 90 | 0.5 | 0.5 |

TABLE V-continued

Selectivity of CARAMBA SL 60 and of Formulation A on wheat plants of the variety "Ralle" after one (*) and two (**) applications

| Application: Track sprayer, 200 l/ha | | Dose rate (g ai/ha) | "Ralle" Necrosis or Chlorosis | |
|---|---|---|---|---|
| | | | 6 d* | 4 d**(=11 d*) |
| | Leaf lamina° | | 0.0 | 1.0 |
| | New leaves°° | | 0.0 | 1.0 |
| Formulation A | Leaf apex° | 180 | 0.0 | 0.3 |
| | Leaf lamina° | | 0.0 | 1.3 |
| | New leaves°° | | 0.3 | 0.3 |
| | Leaf apex° | 90 | 0.0 | 0.0 |
| | Leaf lamina° | | 0.0 | 0.0 |
| | New leaves°° | | 0.0 | 0.0 |

Results and Discussion

The detailed results presented in Tables I to V show that no or insignificant phytotoxicity was observed six days after the first application even at the two fold field rate of both the metconazole formulations.

At four days after the second application (eleven days after the first treatment), Formulation A, applied at twice of the normal field dose rate (2N) and the normal field dose rate (N) was either fully selective or did not cause significant phytotoxicity in the five wheat varieties tested, whereas the CARAMBA SL 60 formulation showed severe phytotoxic symptoms (necrosis or chlorosis) on treated leaves in some cases, in particular at the two-fold field rate, four days after the second application.

The results of the repeated and the higher field application rates show clearly that Formulation A is more selective than CARAMBA SL 60 in wheat.

What is claimed is:

1. A liquid fungicidal composition comprising (a) a fungicidally enhancing amount of a fundicidally acceptable carrier comprising a mixture of 1-pentanol and 2-methylbutanol, wherein the ratio (by weight) of the 1-pentanol to 2-methylbutanol is from 1:1 to 1:10;

(b) a fungicidally effective amount of at least one compound of formula I,

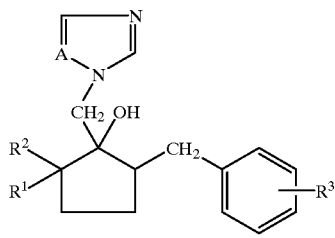

(I)

in which

R$^1$ and R$^2$ each independently represent hydrogen atom or an optionally substituted alkyl, alkenyl, alkynyl or alkadienyl group;

R$^3$ represents a halogen atom or an optionally substituted alkyl, alkenyl, alkynyl, alkadienyl, alkoxy or aryl group;

A represents a nitrogen atom or a CH group; or one of the salts or addition products thereof, which exists in solubilized form;

(c) a solubilizing agent; and (d) optionally other formulation adjuvants.

2. A composition as claimed in claim 1, wherein the compound of formula I is metconazole.

3. A composition as claimed in claim 1, wherein the ratio (by weight) of the 1-pentanol to 2-methylbutanol is from 1:1 to 1:5.

4. A composition as claimed in claim 3, wherein the ratio (by weight) of is the 1-pentanol to 2-methylbutanol from 49:51 to 40:60.

5. A concentrated liquid composition according to claim 1, comprising:

(a) 10%–80% by weight of the carrier, (b) 0.5%–15% by weight of the compound of formula I, (c) 20%–70% by weight of the solubilizing agent, and (d) 0%–10% by weight of the other formulation adjuvants.

6. A concentrated liquid composition according to claim 5, wherein the carrier comprises 5 to 40% by weight of a co-solvent having foam breaking properties; and 10 to 60% by weight an organic solvent consisting essentially of 30 to 50% by weight of 1-pentanol and 50 to 70% by weight of 2-methylbutanol.

7. A concentrated liquid composition according to claim 6, wherein the co-solvent having foam breaking properties is a mixture of aliphatic hydrocarbons.

8. A liquid composition according to claim 1, wherein the composition is essentially free of 3-methylbutanol.

9. A method of controlling the growth of fungi at a locus which comprises applying a fungically effective amount of the composition of claim 1 to the locus.

10. A method of controlling the growth of wheat Septoria spp., Fusarium spp., rust in cereals or wheat powdery mildews at a locus which comprises diluting a concentrated composition as claimed in claim 5 with water and applying said diluted composition to the locus.

* * * * *